United States Patent
Patel et al.

(10) Patent No.: US 10,406,090 B2
(45) Date of Patent: Sep. 10, 2019

(54) ORAL CARE COMPOSITION CONTAINING IONIC LIQUIDS

(71) Applicant: Colgate-Palmolive Company, New York, NY (US)

(72) Inventors: Madhusudan Patel, Somerset, NJ (US); Mahmoud Hassan, Somerset, NJ (US); Rosa Paredes, North Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/654,358

(22) PCT Filed: Dec. 20, 2012

(86) PCT No.: PCT/US2012/070957
§ 371 (c)(1),
(2) Date: Jun. 19, 2015

(87) PCT Pub. No.: WO2014/098869
PCT Pub. Date: Jun. 26, 2014

(65) Prior Publication Data
US 2015/0328113 A1    Nov. 19, 2015

(51) Int. Cl.
| | | |
|---|---|---|
| *A61Q 11/00* | (2006.01) | |
| *A61K 8/41* | (2006.01) | |
| *A61K 8/49* | (2006.01) | |
| *A61K 8/46* | (2006.01) | |
| *A61Q 11/02* | (2006.01) | |

(52) U.S. Cl.
CPC .............. *A61K 8/494* (2013.01); *A61K 8/463* (2013.01); *A61Q 11/00* (2013.01); *A61Q 11/02* (2013.01); *A61K 2800/74* (2013.01)

(58) Field of Classification Search
CPC .... A61K 8/494; A61K 8/463; A61K 2800/74; A61Q 11/00; A61Q 11/02
See application file for complete search history.

(56) References Cited

U.S. PATENT DOCUMENTS

| | | | |
|---|---|---|---|
| 6,165,448 A | | 12/2000 | Joiner et al. |
| 6,544,499 B1 * | | 4/2003 | Glenn, Jr. ............... A61K 8/46 |
| | | | 424/400 |
| 7,939,485 B2 | | 5/2011 | Price et al. |
| 2006/0090777 A1 | | 5/2006 | Hecht et al. |
| 2006/0094617 A1 | | 5/2006 | Price et al. |
| 2006/0189499 A1 | | 8/2006 | Hecht et al. |
| 2006/0251961 A1 * | | 11/2006 | Olbert ..................... B01J 8/067 |
| | | | 429/122 |
| 2008/0214814 A1 | | 9/2008 | Li et al. |
| 2010/0016205 A1 | | 1/2010 | Schwab |

FOREIGN PATENT DOCUMENTS

| | | |
|---|---|---|
| CN | 1433297 | 7/2003 |
| CN | 1859894 | 11/2006 |
| DE | 102005028533 | 12/2006 |
| EP | 2341048 | 3/2013 |
| FR | 2482859 | 11/1981 |
| WO | WO 04/003120 | 1/2004 |
| WO | WO 2006/050299 | 5/2006 |
| WO | WO 06/131234 | 12/2006 |
| WO | WO 09/125222 | 10/2009 |
| WO | WO 10/125302 | 11/2010 |
| WO | WO 2010/141470 | * 12/2010 |
| WO | WO 2011/068815 | * 6/2011 |
| WO | WO 11/087621 | 7/2011 |
| WO | WO 2012/174459 | * 12/2012 |
| WO | WO 14/098867 | 6/2014 |
| WO | WO 14/098868 | 6/2014 |

OTHER PUBLICATIONS

International Search Report and Written Opinion in International Application No. PCT/US2012/070957, dated Oct. 30, 2013.
Written Opinion in International Application No. PCT/US2012/070957.

* cited by examiner

*Primary Examiner* — Lezah Roberts

(57) ABSTRACT

The present invention relation to an oral care composition comprising an ionic liquid wherein the ionic liquid comprises: (a) a pyrazolium cation and (b) an anion selected from the group consisting of acetate, halide, phosphate, alkyl phosphate, sulphate, alkyl sulphate and tosylate is provided.

22 Claims, No Drawings

ORAL CARE COMPOSITION CONTAINING IONIC LIQUIDS

BACKGROUND OF THE INVENTION

An ionic liquid is a class of salt comprising a cation and an anion that is in liquid at a temperature of 100° C. or less and commonly have melting points below room temperature. While not wishing to be bound by theory, ionic liquids generally have much lower symmetry than conventional salts and the charge of cation and anion is distributed over a larger volume of the molecule by resonance in ionic liquids which is thought to contribute to their liquid state at much lower temperatures than conventional salts (e.g. NaCl, mp 801° C.). Ionic liquids are often composed of a cation comprising a heterocyclic ring and a counter anion, often inorganic in nature. The nature of the cation and anion will determine the hydrophobicity, viscosity, density and other physical parameters and properties of the ionic liquid.

Ionic liquids have been evaluated as environmentally-friendly or 'green' alternatives to conventional organic solvents for a wide range of organic synthetic applications. Ionic liquids have unique characteristics that distinguish them from conventional organic solvents. For example, ionic liquids are non-volatile (i.e. they do not evaporate readily into the atmosphere), they have a high polarity and charge density, they may be hydrophobic or hydrophilic, and they have unique solvating properties. As such, ionic liquids are known to be used in cleaning compositions (for example, as disclosed in US 2006/0090777 A1 and U.S. Pat. No. 7,939,485 B2). A range of ionic liquids are commercially available, or they may be readily synthesized by simple ion-exchange reactions.

It is seen as being desirable by consumers to possess white teeth. Over time, teeth can darken or become stained. Teeth naturally become more yellow with age and can also be stained by food and drink. For example, teeth can be stained by tea, coffee, red wine and tobacco. Certain antibiotics, including for example tetracycline, can also stain teeth. Many consumers wish to whiten teeth to restore the natural colour and in some circumstances wish to whiten teeth beyond their natural colour.

It is known to use peroxide-based chemicals to whiten teeth. Carbamide peroxide can be used to bleach teeth. Carbamide peroxide generates hydrogen peroxide upon contact with water and the peroxide oxidizing agent bleaches stains. Whitening can be carried out by a dental professional, by a non-dental professional such as a beauty therapist or alternatively at home by the consumer themselves. Professional tooth whitening is expensive and time consuming.

However, peroxide compounds are highly reactive, and consequently difficult to formulate. Moreover, hydrogen peroxide can spontaneously decompose to form oxygen gas ($O_2$) and water, so that on storage, the dentifrice containers may bloat, burst or leak, and the remaining formulation will not have enough peroxide remaining to clean and whiten teeth effectively. Some initially comprise very high levels of peroxide, which decomposes over time, so that the exact amount of peroxide delivered on application is variable and largely depends on how long and under what conditions the dentifrice has been stored.

Teeth can also be whitened and stains removed using abrasive agents to physically remove stains from the teeth. Abrasive agents can include baking soda (sodium bicarbonate), silica, aluminium oxide, calcium carbonate and calcium phosphate. However, abrasive agents can cause damage to the tooth enamel and can be especially damaging to softened tooth enamel that has become soft with age or with repeated attack with oral acids or the use of acidic foods and beverages. Furthermore, abrasive agents are not always suitable for whitening the teeth of those consumers who have dentures, crowns or who wear orthodontics. For these consumers, abrasive whitening agents can damage the ceramic surfaces or may not provide effective reach to clean between orthodontic wiring.

A biofilm is a structured group of microorganisms encapsulated within a self-developed polymeric extracellular matrix. Biofilms are typically adhered to a living or inert surface. In the human or animal body biofilms can form on any internal or external surface. Biofilms have been found to be involved in a wide variety of microbial infections in the body and cause a number of conditions including urinary tract infections, middle-ear infections, and in particular, diseases of the oral cavity.

Dental plaque is formed from a biofilm precursor, and is present to some degree on virtually all dental surfaces. It comprises a dense microbial layer consisting of a mass of microorganisms embedded in a polysaccharide matrix. Plaque may form on any part of the tooth surface, and is found particularly at the gingival margin, and in cracks in the enamel. The danger associated with the formation of plaque on the teeth lies in the tendency of plaque to build up and eventually produce gingivitis, periodontitis and other types of periodontal disease, as well as dental caries and dental calculus.

Plaque itself adheres very firmly to dental surfaces and rapidly reforms on the tooth surface after it is removed. Current plaque removal methods rely primarily on the mechanical removal of plaque. These methods, which include brushing, brushing with an abrasive toothpaste, flossing, using interdental cleaners, scraping, using sonic energy (e.g. Sonicare toothbrushes) and ultrasound (e.g. Ultreo toothbrushes), in part, rely on a good brushing or flossing technique which may consumers simply do not possess. Moreover, these methods are particularly inefficient in removing stubborn plaque, or plaque hidden deep within cavities and fissures of teeth, or within gum pockets.

It is also known in the art to incorporate antimicrobial agents in oral compositions which destroy or retard the growth of bacteria. However, bacteria present in a biofilm or plaque deposit exhibit increased resistance to antimicrobial agents because the dense extracellular matrix and the outer layer of cells protect the bacteria found in the interior of the deposit from the effects of the antimicrobial agents.

It would be desirable to provide improved methods and compositions for whitening teeth that can achieve whitening benefits without damaging tooth enamel. It would also be desirable to provide improved methods and compositions for whitening the teeth of consumers who possess dentures, crowns or who wear orthodontics.

SUMMARY OF THE INVENTION

The present invention aims at least partially to meet these needs in the art. Further embodiments of the invention will be apparent from the detailed description and the examples According to a first aspect of the invention there is provided an oral care composition comprising an ionic liquid wherein the ionic liquid comprises a) a pyrazolium cation b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate.

Optionally, the pyrazolium cation is substituted with at least one alkyl group. Optionally, the pyrazolium cation is a pyrazolium cation of formula

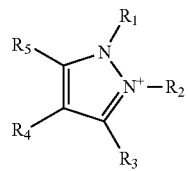

wherein substituents $R_1$, $R_2$, $R_3$, $R_4$ and $R_5$ are the same or different and are independently selected from H and $C_1$-$C_{10}$ alkyl groups.

Optionally, any one of $R_1$, $R_2$, $R_3$, $R_4$ and $R_5$ is a $C_1$-$C_4$ alkyl group. Further optionally any two of $R_1$, $R_2$, $R_3$, $R_4$ and $R_5$ are $C_1$-$C_4$ alkyl groups. Further optionally any three of $R_1$, $R_2$, $R_3$, $R_4$ and $R_5$ are $C_1$-$C_4$ alkyl groups.

Optionally, any one of $R_1$, $R_2$, $R_3$, $R_4$ and $R_5$ is a methyl group. Further optionally any two of $R_1$, $R_2$, $R_3$, $R_4$ and $R_5$ are methyl groups. Further optionally any three of $R_1$, $R_2$, $R_3$, $R_4$ and $R_5$ are methyl groups.

Optionally, $R_1$, $R_2$ and $R_4$ are $C_1$-$C_4$ alkyl and $R_3$ and $R_5$ are H.

Optionally the pyrazolium cation is 1,2,4-trimethylpyrazolium

Optionally the anion is an alkyl sulphate. Further optionally, the anion is methylsulfate.

Optionally the ionic liquid is 1,2,4-trimethylpyrazolium methylsulfate.

Optionally the ionic liquid is present in an amount from about 0.1 weight % to about 30 weight % based on the total weight of the composition. Optionally the ionic liquid is present in an amount from about 5 weight % to about 30 weight %, about 10 weight % to about 25 weight %, about 15 weight % to about 25 weight % or about 18 weight % to about 22 weight % based on the total weight of the composition.

Optionally, the oral care composition comprises an abrasive in an amount of less than 0.1 weight % by total weight of the composition Further optionally, the composition comprises an abrasive in an amount of less 0.01% by total weight of the composition. Optionally, the oral care composition is substantially free of any abrasives.

Optionally, the oral care composition comprises a PVP-peroxide compound in an amount of less than about 0.1 weight % by total weight of the composition Further optionally the composition comprises a peroxide compound in an amount of less about 0.01% by total weight of the composition. Optionally, the oral care composition is substantially free of any peroxide compound.

Optionally the composition further comprises an orally acceptable carrier. Optionally the orally acceptable carrier is an orally acceptable carrier for a mouth rinse, toothpaste, oral beads or strips, irrigation fluid, plaque removal liquid, tongue spray, dental floss, candy, lozenge, chewing, patch (e.g. intra oral patch similar to smokeless tobacco pouches) or lollipop. Further optionally, the ionic liquid is formulated into a mouth rinse with the mouth rinse optionally containing compatible ingredients such as glycerin, sorbitol, propylene glycol.

Optionally the composition may comprise one or more agents selected from diluents, bicarbonate salts, pH modifying agents, surfactants, foam modulators, thickening agents, viscosity modifiers, humectants, sweeteners, flavorants, pigments, anticaries agents, anticalculus or tartar control agents, abrasives and mixtures thereof.

Optionally, the oral care composition is for teeth whitening.

According to a further aspect of the invention there is provided a method of whitening teeth in a subject comprising administering a therapeutically effective amount of a composition comprising an ionic liquid to the subject wherein the ionic liquid comprises:

a) a pyrazolium cation b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate Optionally, the pyrazolium cation is substituted with at least on alkyl group. Further optionally the pyrazolium cation is a pyrazolium cation of formula

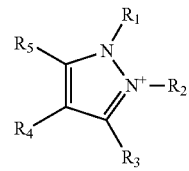

wherein substituents $R_1$, $R_2$, $R_3$, $R_4$ and $R_5$ are the same or different and are independently selected from H and $C_1$-$C_{10}$ alkyl groups.

Optionally, any one of $R_1$, $R_2$, $R_3$, $R_4$ and $R_5$ is a $C_1$-$C_4$ alkyl group. Further optionally any two of $R_1$, $R_2$, $R_3$, $R_4$ and $R_5$ are $C_1$-$C_4$ alkyl groups. Further optionally any three of $R_1$, $R_2$, $R_3$, $R_4$ and $R_5$ are $C_1$-$C_4$ alkyl groups. Optionally, any one of $R_1$, $R_2$, $R_3$, $R_4$ and $R_5$ is a methyl group. Further optionally, any two of $R_1$, $R_2$, $R_3$, $R_4$ and $R_5$ are methyl groups. Further optionally any three of $R_1$, $R_2$, $R_3$, $R_4$ and $R_5$ are methyl groups. Further optionally $R_1$, $R_2$ and $R_4$ are $C_1$-$C_4$ alkyl and $R_3$ and $R_5$ are H.

Optionally the pyrazolium cation is 1,2,4-trimethylpyrazolium

Optionally the pyrazolium cation is 1,2,4-trimethylpyrazolium

Optionally the anion is an alkyl sulphate. Further optionally the anion is methylsulfate.

Optionally the ionic liquid is 1,2,4-trimethylpyrazolium methylsulfate.

Optionally the ionic liquid is present in an amount from about 0.1 weight % to about 30 weight %, about 5 weight % to about 30 weight %, about 10 weight % to about 25 weight %, about 15 weight % to about 25 weight % or about 18 weight % to about 22 weight % based on the total weight of the composition.

Optionally the composition comprises an abrasive in an amount of less than about 0.1 weight % by total weight of the composition or less 0.01% by total weight of the composition. Further optionally the composition is substantially free of any abrasives.

Optionally the composition comprises a peroxide compound in an amount of less than 0.1 weight % or less than 0.01% by total weight of the composition. Further optionally the composition is substantially free of any peroxide compound.

Optionally the composition further comprises an orally acceptable carrier. Further optionally the oral care composition further comprises an orally acceptable carrier for a mouth rinse, toothpaste, oral beads or strips, irrigation fluid, plaque removal liquid, tongue spray, dental floss, candy, lozenge, chewing or lollipop.

Optionally the composition further comprises one or more agents selected from diluents, bicarbonate salts, pH modifying agents, surfactants, foam modulators, thickening agents, viscosity modifiers, humectants, sweeteners, flavorants, pigments, anticaries agents, anticalculus or tartar control agents, abrasives and mixtures thereof.

According to a further aspect of the invention there is provided use of an ionic liquid in an oral care composition for whitening teeth in the oral cavity of a subject wherein the ionic liquid comprises:
a) a pyrazolium cation
b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate

DESCRIPTION OF THE INVENTION

It should be understood that the detailed description, and specific examples, while indicating embodiments of the invention, are intended for purposes of illustration only and are not intended to limit the scope of the invention.

As used throughout, ranges are used as shorthand for describing each and every value that is within the range. Any value within the range can be selected as the terminus of the range.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition, unless otherwise specified.

In some embodiments, the present invention provides an oral care composition comprising an ionic liquid, wherein the ionic liquid comprises:
a) a pyrazolium cation, and
b) an anion selected from the group consisting of acetate, halide, phosphate, alkyl phosphate, sulfate, alkyl sulfate, and tosylate.

Pyrazolium

A "pyrazolium" cation as used in the context of the present invention, has the general basic ring structure of Formula 1, and optionally has substituents including H, alkyl, alkenyl or aryl at positions $R_1$ to $R_5$.

Formula 1:

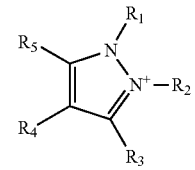

In some embodiments, $R_1$, $R_2$, $R_3$, $R_4$ and $R_5$ are independently selected from H, alkyl and alkenyl.

As used herein, the term "alkyl" refers to a saturated aliphatic hydrocarbon, including straight-chain, branched-chain and cycloalkyl groups of 1 to 20 carbon atoms. Alkyl groups include methyl, ethyl, propyl, butyl, pentyl, hexyl, heptyl, octyl, nonyl and decyl. The alkyl or alkenyl groups mentioned herein may be linear or branched. Typically, the alkyl or alkenyl groups are linear. As used herein, the term "cycloalkyl" refers to a $C_{3-8}$ cyclic hydrocarbon. As used herein, the term "alkenyl" refers to an unsaturated, open chain hydrocarbon with 2 to 20 carbon atoms and with one or more carbon-carbon double bonds. For example, alkenyl groups include allyl and vinyl.

In some embodiments $R_1$, $R_2$, $R_3$, $R_4$ and $R_5$ are the same or different and are independently selected from H and $C_1$-$C_{10}$ alkyl groups.

In some embodiments, $R_3$ and $R_5$ are H and $R_1$, $R_2$ and $R_4$ are independently selected from alkyl and alkenyl. $R_1$, $R_2$ and $R_4$ may be the same or different. Optionally, $R_3$ and $R_5$ are H and $R_1$, $R_2$ and $R_4$ are $C_{14}$ alkyl In a preferred embodiment, $R_1$, $R_2$ and $R_4$ are methyl. Typically, $R_3$ and $R_5$ are H.

In a typical embodiment, $R_1$, $R_2$ and $R_4$ are methyl, ethyl, propyl, or butyl, and $R_3$ and $R_5$ are H.

Anions

As used herein, the term "halide" refers to Fl, Cl, Br, I. In some embodiments, the anion is a halide selected from Br and Cl.

As used herein, the term "alkyl" is refers to a saturated aliphatic hydrocarbon, including straight-chain, branched-chain and cycloalkyl groups of 1 to 20 carbon atoms.

In some embodiments, the anion is an alkyl sulfate selected from methyl sulfate, ethyl sulfate, propyl sulfate, butyl sulfate, pentyl sulfate, hexyl sulfate, heptyl sulfate, and octyl sulfate. In a preferred embodiment, the anion is methyl sulfate.

In some embodiments, the alkyl sulfate and alkyl phosphate comprise from 1 to 22 carbon atoms. Optionally, the alkyl sulfate and alkyl phosphate comprise 1 to 4 carbon atoms, or 6 to 10 carbon atoms or 12 to 22 carbon atoms Typically, the anion is selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate.

In preferred embodiments, the anion is selected from the group consisting of methyl sulfate, ethyl sulphate and octyl sulfate. In another embodiment, the anion is bromide. In a further embodiment, anion is diethylphosphate. In yet a further embodiment, the anion is tosylate. In still yet a further embodiment, the anion is acetate.

Ionic Liquid

The term "ionic liquid" used in the context of the present invention means a salt comprising a cation and an ion that is in liquid at a temperature of 100° C. or less and commonly have melting points below room temperature. Any anion mentioned above may be used in combination with any of the pyrazolium ions defined above to form the oral care composition of the present invention.

A particularly preferred ionic liquid is 1,2,4-trimethyl-pyrazolium methyl sulphate, Formula 2:

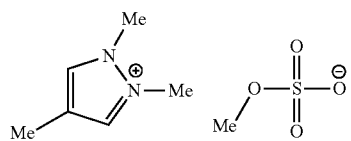 [SMILES: Cc1cn(C)[n+](C)c1 ; COS(=O)(=O)[O-]]

Typically, the ionic liquid is present in the oral care composition in an amount of about 0.1 wt % to about 30 wt % based on the total weight of the composition.

In some embodiments, the ionic liquid is present in the oral care composition in an amount of about 0.5 wt % to about 20 wt %, or from about 1 wt % to about 15 wt %, based on the total weight of the composition. Optionally, the ionic liquid is present in the oral care composition in an amount of about 5 wt % to about 20 wt %, or from about 5 wt % to about 15 wt %, or from about 7 wt % to about 12 wt %, based on the total weight of the composition.

Preferably, the ionic liquid is present in the oral care composition in an amount of about 8 wt % to about 10 wt % based on the total weight of the composition.

In some embodiments, the ionic liquid is present in the oral care composition in a concentration of about 1 mM to about 500 mM, or from about 4 mM to about 400 mM.

Optionally, the ionic liquid is present in the oral care composition in a a concentration of about 5 mM to about 300 mM or from about 10mM to about 270 mM Preferably, the ionic liquid is present in the oral care composition in a concentration of about 15 mM to about 20 mM, or from about 18 mM to about 22 mM or about 1 mM to about 50 mM.

Abrasives

Whilst the compositions of the present invention may optionally further comprise an abrasive which may be useful, for example, as a polishing agent, it has been found that oral care compositions comprising ionic liquids as defined herein, are effective in removing biofilm or plaque, and whitening teeth, without the need for substantial amounts of abrasives. This is advantageous because abrasives can damage enamel and expose dentine tissues with repeated use, particularly, in subjects with soft enamel caused by disease or excessive exposure to food acids.

In one embodiment, the oral care composition comprises an abrasive in an amount of less than 0.1 wt % by total weight of the composition. In another embodiment, the oral care composition comprises an abrasive in an amount of less than 0.01 wt % by total weight of the composition. In yet another embodiment, the composition is substantially free, or free, of any abrasives.

Suitable optional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

Carrier

Among useful carriers for optional inclusion in a composition of the invention are diluents, bicarbonate salts, pH modifying agents, surfactants, foam modulators, thickening agents, viscosity modifiers, humectants, sweeteners, flavorants, pigments, anticaries agents, and anticalculus or tartar control agents, abrasives or mixtures thereof. Carriers should be selected for compatibility with each other and with other ingredients of the composition.

Water is a preferred diluent and in some compositions such as mouthwashes, water is commonly accompanied by an alcohol, e.g., ethanol. The weight ratio of water to alcohol in a mouthwash composition is generally 1:1 to 20:1, for example 3:1 to 20:1 or 4:1 to 10:1. In a whitening liquid, the weight ratio of water to alcohol can be within or below the above ranges, for example, 1:10 to 2:1.

In a further embodiment, the composition of the invention comprises at least one bicarbonate salt, useful for example to impart a "clean feel" to teeth and gums due to effervescence and release of carbon dioxide. Any orally acceptable bicarbonate can be used, including without limitation, alkali metal bicarbonates such as sodium and potassium bicarbonates, ammonium bicarbonate and the like. One or more bicarbonate salts are optionally present in a total amount of about 0.1 wt % to about 50 wt %, for example about 1 wt % to 20 wt %, by total weight of the composition.

In a still further embodiment, the composition of the invention comprises at least one pH modifying agent. Such agents include acidifying agents to lower pH, basifying agents to raise pH, and buffering agents to control pH within a desired range. For example, one or more compounds selected from acidifying, basifying and buffering agents can be included to provide a pH of 2 to 10, or in various illustrative embodiments, 2 to 8, 3 to 9, 4 to 8, 5 to 7, 6 to 10, 7 to 9, etc. Any orally acceptable pH modifying agent can be used, including without limitation, carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an orally acceptable pH range.

In a still further embodiment, the composition of the invention comprises at least one surfactant. Any orally acceptable surfactant, most of which are anionic, nonionic or amphoteric, can be used. Suitable anionic surfactants include without limitation, water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation, poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation, derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of about 0.01 wt % to about 10 wt %, for example, from about 0.05 wt % to about 5 wt %, or from about 0.1 wt % to about 2 wt % by total weight of the composition.

In a still further embodiment, the composition of the invention comprises at least one foam modulator, useful for example to increase amount, thickness or stability of foam generated by the composition upon agitation. Any orally acceptable foam modulator can be used, including without limitation, polyethylene glycols (PEGs), also known as polyoxyethylenes. High molecular weight PEGs are suitable, including those having an average molecular weight of 200,000 to 7,000,000, for example 500,000 to 5,000,000, or 1,000,000 to 2,500,000. One or more PEGs are optionally present in a total amount of about 0.1 wt % to about 10 wt %, for example from about 0.2 wt % to about 5 wt %, or from about 0.25 wt % to about 2 wt %, by total weight of the composition.

In a still further embodiment, the composition of the invention comprises at least one thickening agent, useful for example to impart a desired consistency and/or mouth feel to the composition. Any orally acceptable thickening agent can be used, including without limitation, carbomers, also known as carboxyvinyl polymers, carrageenans, also known as Irish moss and more particularly t-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. A preferred class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred Carbopols include Carbopol 934, 940, 941, 956, 974P, and mixtures thereof. One or more thickening agents are optionally present in a total amount of from about 0.01 wt % to 15 wt %, for example from about 0.1 wt % to about 10 wt %, or from about 0.2 wt % to about 5 wt %, by total weight of the composition.

In a still further embodiment, the composition of the invention comprises at least one viscosity modifier, useful for example to inhibit settling or separation of ingredients or to promote re-dispersibility upon agitation of a liquid composition. Any orally acceptable viscosity modifier can be used, including without limitation, mineral oil, petrolatum, clays and organomodified clays, silica and the like. One or more viscosity modifiers are optionally present in a total amount of from about 0.01 wt % to about 10 wt %, for example, from about 0.1 wt % to about 5 wt %, by total weight of the composition.

In a still further embodiment, the composition of the invention comprises at least one humectant. Any orally acceptable humectant can be used, including without limitation, polyhydric alcohols such as glycerin, sorbitol, xylitol or low molecular weight PEGs. Most humectants also function as sweeteners. One or more humectants are optionally present in a total amount of from about 1 wt % to about 70 wt %, for example, from about 1 wt % to about 50 wt %, from about 2 wt % to about 25 wt %, or from about 5 wt % to about 15 wt %, by total weight of the composition.

In a still further embodiment, a composition of the invention comprises at least one sweetener, useful for example to enhance the taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, cyclamates and the like. One or more sweeteners are optionally present in a total amount depending strongly on the particular sweetener(s) selected, but typically 0.005 wt % to 5 wt %, by total weight of the composition.

In a still further embodiment, a composition of the invention comprises at least one flavorant, useful for example to enhance taste of the composition. Any orally acceptable natural or synthetic flavorant can be used, including without limitation vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, a-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of from about 0.01 wt % to about 5 wt %, for example, from about 0.1 wt % to about 2.5wt %, by total weight of the composition.

In a still further embodiment, a composition of the invention may comprise at least one colorant. Colorants herein include pigments, dyes, lakes and agents imparting a particular luster or reflectivity such as pearling agents. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. One or more colorants are optionally present in a total amount of from about 0.001 wt % to about 20 wt %, for example, from about 0.01 wt % to about 10 wt %, or from about 0.1 wt % to about 5 wt %, by total weight of the composition.

In some embodiments, the composition comprises a fluoride ion source. Fluoride ion sources include, but are not limited to: stannous fluoride, sodium fluoride, potassium fluoride, potassium monofluorophosphate, sodium monofluorophosphate, ammonium monofluorophosphate, sodium fluorosilicate, ammonium fluorosilicate, amine fluoride such as olaflur (N'-octadecyltrimethylendiamine-N,N,N'-tris(2-ethanol)-dihydrofluoride), ammonium fluoride, and combinations thereof. In certain embodiments the fluoride ion source includes stannous fluoride, sodium fluoride, amine fluorides, sodium monofluorophosphate, as well as mixtures thereof. In certain embodiments, the oral care composition of the invention may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions of the invention at a level of about 0.001 wt % to about 10 wt %, e.g., from about 0.003 wt % to about 5 wt %, 0.01 wt % to about 1 wt, or about 0.05 wt %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

The composition of the present invention optionally comprises a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The composition of the present invention optionally incorporates one or more antisensitivity agents, e.g., potassium salts such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, e.g., from about 1 wt % to about 20 wt % by weight based on the total weight of the composition, depending on the agent chosen. The compositions of the present invention may also be used to treat hypersensitivity by blocking dentin tubules when applied to a tooth.

In some embodiments, the composition of the invention further comprises an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

In another embodiment, the composition comprises an orally acceptable zinc ion source useful, for example, as an antimicrobial, anticalculus or breath-freshening agent. One or more such sources can be present. Suitable zinc ion sources include without limitation zinc acetate, zinc citrate, zinc gluconate, zinc glycinate, zinc oxide, zinc sulfate, sodium zinc citrate and the like. One or more zinc ion sources are optionally and illustratively present in a total amount of from about 0.05 wt % to about 3 wt %, for example from about 0.1 wt % to about 1 wt %, by total weight of the composition.

The composition of the present invention may additionally optionally comprise a tartar control (anticalculus) agent as provided below. Tartar control agents among those useful herein include salts of the specified agents, including alkali metal and ammonium salts. The agents include: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®.

In some embodiments, the composition of the present invention further comprises a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophan, L-lysine, methionine, threonine, levocarnitine and L-carnitine), lipotropics (such as choline, inositol, betaine, and linoleic acid), and mixtures thereof.

In some embodiments, the oral care composition of the invention does not contain any other antibacterial or whitening agent.

Delivery

The oral care composition of the present invention preferably comprises an orally acceptable carrier for use in a product such as a mouth rinse (including dual phase mouthwash), toothpaste, actives in beads/strips, irrigation fluids, plaque removal fluids, bead formulas, formulations to be delivered through devices such as pens, back of a toothbrush and front of a toothbrush, formulations to be delivered through porous wicking materials, interdental brushes, fluid encased dental strips, floss impregnated or coated with the formulations or dried formulations, portables, oral trays, hard or soft candy, lozenge with a soft plaque dissolving liquid inside, lollipops with the plaque dissolving formulation imbedded into the lickable "candy" that can also help control tongue bacteria, peelable gels, patches, formulations for pop-rocks that upon popping, spread a fine mist of the formulation around oral cavity, tongue cleaners with plaque dissolving strips and dental strips. Accordingly, opportunities exist for professional use of the compositions of the present invention (e.g. during cleanings, irrigations, or aggressive periodontal procedures, such as root planning & scaling). The composition of the invention may be provided in any of the products defined herein. If used in animals or pets, veterinary pastes, chewables or treats may also be used as the orally acceptable carrier.

In one embodiment, the composition of the invention can be dried into powder and utilized in a portable sachet. For example, upon mixing such a powder with a suitable solvent such as water, a rinse may be created to remove plaque, proteins and other debris in the mouth.

In another embodiment, the composition of the invention can be dried with abrasives such as silica, calcium carbonate or soft capsules that upon addition of small amount of water, creates a paste.

Formulations that increase the substantivity of ionic liquids onto a surface could be expected to increase the efficacy of biofilm, and hence plaque removal. For example, Tween 20 while also functioning as a surfactant, is also a wetting agent. Therefore, incorporation of such an agent could be expected to increase the wettability and spreading of a mouth rinse formulation according to the present invention, over the soft and hard tissue, increasing the formulation's propensity for plaque dissolution and removal.

Methods of Use

The composition according to the present invention may be administered to or applied to a human or other animal subject. The composition may be suitable for administration or application to the oral cavity of a human or animal subject. Typically, the composition is for whitening teeth and/or removing tooth stains. The composition may also dissolve plaque. Furthermore, the reduction or removal of plaque may occur through an inhibition of biofilm (a plaque precursor) formation and/or degradation of microbial biofilm. The present invention provides a method of whitening teeth in a subject comprising administering a therapeutically effective amount of a composition comprising an ionic liquid to the subject wherein the ionic liquid comprises a pyrazolium cation and an anion selected from the group consisting of acetate, halide, phosphate, alkyl phosphate, sulphate, alkyl suphate and tosylate. Preferably, the composition is an oral care composition as defined herein, and the composition is applied to the oral cavity.

The present invention further provides a use of an ionic liquid, in an oral care composition, for whitening teeth in the oral cavity of a subject. The oral care composition is preferably as defined herein.

Compositions comprising an ionic liquid are highly effective in inhibiting the growth of bacteria, degrading biofilms, and dissolving dental plaque. They possess the unique ability to offer a deep but gentle cleaning, and promote removal of biofilm and plaque without the need for harsh abrasives or rigorous brushing. The compositions are further able to remove stains and whiten teeth, again without the need for harsh abrasives or rigorous brushing. In particular, ionic liquids are highly effective in whitening artificially stained human teeth when formulated into a mouth rinse.

The invention is further illustrated in the following non-limiting examples.

EXAMPLES

Compositions with Ingredient Ranges for a Whitening Mouth Rinse containing 1,2,4-Trimethylpyrazolium methylsulfate (Table 1):

TABLE 1

| Ingredient Name | Level Range |
|---|---|
| Glycerin | 0-20 |
| Propylene Glycol | 0-10 |
| Sorbitol | 0-20 |
| 1,2,4-Trimethylpyrazolium methylsulfate | 5-20 |
| Na Benzoate | 0-0.11 |
| CPC | 0-0.075 |
| Surfactant* | 1.5 |
| Sucralose | 0.05 |
| Citrate Buffer | 10 |
| Flavor | 0.15 |
| Water | q.s |

*Polysorbate 20, Polysorbate 80, Pluronic F-108, Pluronic F-127, PEG40

Table 1 provides details of typical compositions for a mouth rinse comprising 1,2,4-trimethylpyrazolium methylsulfate. These amounts are weight percentages based on the total weight of the composition.

Three example compositions were tested in order to determine the whitening efficacy. The determination of the whitening efficacy was conducted as follows: After brushing and rinsing, the artificially stained human teeth were allowed to dry and the initial L*a*b* readings recorded (L*a*b* refers to stain score in accordance with the Commission International de L'Eclairage Laboratory (CIELAB) color scale. L* (lightness-darkness scale), a* (red-green chroma) and b* (yellow-blue chroma)). The teeth were then soaked for 28 treatments at 2 minutes per treatment in 1 mL of the prototype whitening mouth rinse. The noted treatment time is typically used to equate 2 weeks' worth of consumer usage when brushing. The teeth were rinsed with DI water after every treatment. The whitening solutions were replenished every $7^{th}$ treatment. After 28 treatments, the teeth were rinsed with distilled water and allowed to dry. The final L*a*b* readings were then recorded. Whitening values were calculated using Equation 1: $\Delta W^* = W^*_{final} - W^*_{initial}$ (where $W^* = (a^{*2} + b^{*2} + (L^* - 100)^2)^{1/2} - \Delta W^*$ (whitening) is used for quantifying the whitening efficacy of each formula.

Mouth Rinse Compositions with their respective whitening efficacies, ΔW and ΔL (Table 2):

TABLE 2

| | Ingredient Level | | | | |
|---|---|---|---|---|---|
| Ingredient Name | A | B | C | Hydrogen peroxide formulation | Stain guard formulation |
| Glycerin | 0 | 0 | 10 | | |
| Propylene Glycol | 0 | 2.5 | 7 | | |
| Sorbitol | 20 | 10 | 2 | | |
| 1,2,4-Trimethylpyrazolium methylsulfate | 20 | 20 | 20 | | |
| Na Benzoate | 0.11 | 0.11 | 0.11 | | |
| CPC | 0.075 | 0.075 | 0.075 | | |
| Surfactant | Tween 20 | Tween 20 | Tween 20 | | |
| pH | 4 | 5 | 5 | | |
| ΔW | −23.54 | −25.29 | −21.05 | −19.22 | 1.68 |
| ΔL | 25.17 | 26.48 | 22.50 | 17.34 | −2.5 |

Tween 20 (polyoxyethylene sorbitan monolaurate)

The results of the whitening analysis are given in Table 2. The more negative the change in Whiteness, ΔW, the whiter the appearance of teeth. The more positive and greater the ΔL value, the lighter the colour of the teeth. The compositions were compared to hydrogen peroxide containing whitening formulation and a formulation with stain guard technology to prevent stains from attaching to the surface of the teeth.

As can be seen compositions A, B and C all provided greater whitening efficacy than previously known whitening formulations.

We claim:

1. A teeth-whitening oral care composition comprising an ionic liquid
    wherein the ionic liquid comprises
    a) a pyrazolium cation; b) an anion selected from the group consisting of salicylate, acetate, bromide, chloride, phosphate, alkyl phosphate, phosphonate, pyrophosphate, hexametaphosphate, polymetaphosphate, orthophosphate, tripolyphosphate, sulfate, alkyl sulfate, lauryl sulfate, phenolsulfate, benzoate, acetylacetonate, carboxylate, citrate, ascorbate, dicyamide, L- or D-amino acids, glycolate, gluconate, maleate, saccharinate, aspartamate, cyclamate, hydroxide, succinate, tartrate, docusate, linoleate, oleate, and tosylate; and c) an orally acceptable carrier,
        wherein the orally acceptable carrier comprises at least one of glycerine, propylene glycol and sorbitol, and wherein the ionic liquid is present in an amount from 15 weight % to 25 weight % based on the total weight of the composition;
        wherein the pyrazolium cation is a pyrazolium cation of formula

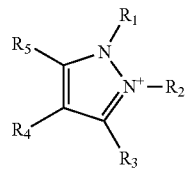

wherein substituents $R_1$, $R_2$, $R_3$, $R_4$ and $R_5$ are the same or different and are independently selected from H and $C_1$-$C_{10}$ alkyl groups.

2. The oral care composition of claim 1 wherein the pyrazolium cation is substituted with at least one alkyl group.

3. The oral care composition of claim 1 wherein any one of $R_1$, $R_2$, $R_3$, $R_4$ and $R_5$ is a $C_1$-$C_4$ alkyl group.

4. The oral care composition of claim 1 wherein any two of $R_1$, $R_2$, $R_3$, $R_4$ and $R_5$ are $C_1$-$C_4$ alkyl groups.

5. The oral care composition of claim 1 wherein any three of $R_1$, $R_2$, $R_3$, $R_4$ and $R_5$ are $C_1$-$C_4$ alkyl groups.

6. The oral care composition of claim 1 wherein any one of $R_1$, $R_2$, $R_3$, $R_4$ and $R_5$ is a methyl group.

7. The oral care composition of claim 1 wherein any two of $R_1$, $R_2$, $R_3$, $R_4$ and $R_5$ are methyl groups.

8. The oral care composition of claim 1 wherein any three of $R_1$, $R_2$, $R_3$, $R_4$ and $R_5$ are methyl groups.

9. The oral care composition of claim 1 wherein $R_1$, $R_2$ and $R_4$ are $C_1$-$C_4$ alkyl and $R_3$ and $R_5$ are H.

10. The oral care composition of claim 1 wherein the pyrazolium cation is 1,2,4-trimethylpyrazolium.

11. The oral care composition of claim 1 wherein the anion is an alkyl sulphate.

12. The oral care composition of claim 1 wherein the anion is methylsulfate.

13. The oral care composition of claim 1 wherein the ionic liquid is 1,2,4-trimethylpyrazolium methylsulfate.

14. The oral care composition of claim 1 wherein the ionic liquid is present in an amount from 18 weight % to 22 weight % based on the total weight of the composition.

15. The oral care composition of claim 1 wherein the composition comprises an abrasive in an amount of less than 0.1 weight % by total weight of the composition.

16. The oral care composition of claim 1 wherein the composition comprises an abrasive in an amount of less than 0.01 weight % by total weight of the composition.

17. The oral care composition of claim 1 wherein the composition is substantially free of any abrasives.

18. The oral care composition of claim 1 wherein the composition comprises a peroxide compound in an amount of less than 0.1 weight % by total weight of the composition.

19. The oral care composition of claim 1 wherein the composition comprises a peroxide compound in an amount of less than 0.01 weight % by total weight of the composition.

20. The oral care composition of claim 1 wherein the composition is substantially free of any peroxide compound.

21. The oral care composition of claim 1 wherein the oral care composition further comprises an orally acceptable carrier for a mouth rinse, toothpaste, oral beads or strips, irrigation fluid, plaque removal liquid, tongue spray, dental floss, candy, lozenge, chewing or lollipop.

22. The oral care composition of claim 1 wherein the composition further comprises one or more agent selected from diluents, bicarbonate salts, pH modifying agents, surfactants, foam modulators, thickening agents, viscosity modifiers, humectants, sweeteners, flavorants, pigments, anticaries agents, anticalculus or tartar control agents, abrasives and mixtures thereof.

* * * * *